United States Patent [19]
Antonetti

[11] Patent Number: 5,496,303
[45] Date of Patent: Mar. 5, 1996

[54] TRANSFUSION AND PERFUSION DEVICE FOR DRIP AND/OR EMERGENCY INTERVENTION

[76] Inventor: Pierre Antonetti, 7, avenue Jean Jaurès, F-06540 Bresil-sur-Roya, France

[21] Appl. No.: 211,095
[22] PCT Filed: Sep. 17, 1992
[86] PCT No.: PCT/FR92/00870
  § 371 Date: Mar. 18, 1994
  § 102(e) Date: Mar. 18, 1994
[87] PCT Pub. No.: WO93/05831
  PCT Pub. Date: Apr. 1, 1993

[30] Foreign Application Priority Data
Sep. 18, 1991 [FR] France .................. 91 11594

[51] Int. Cl.⁶ .................. A61B 19/00; A61M 37/00
[52] U.S. Cl. .................. 604/410; 604/140; 604/144; 604/174; 604/179; 128/DIG. 6; 128/DIG. 12
[58] Field of Search .................. 604/131, 134, 604/140–144, 174, 179, 257, 408, 410; 128/DIG. 6, DIG. 12; 222/92, 94–96, 107

[56] References Cited

U.S. PATENT DOCUMENTS

| | | | |
|---|---|---|---|
| 4,326,526 | 4/1982 | Buck et al. | 604/410 |
| 4,430,078 | 2/1984 | Sprague | 604/141 |
| 4,666,430 | 5/1987 | Brown et al. | 604/141 |
| 5,368,570 | 11/1994 | Thompson et al. | 604/142 |

FOREIGN PATENT DOCUMENTS

| | | |
|---|---|---|
| 0210424 | 2/1987 | European Pat. Off. . |
| 0265261 | 4/1988 | European Pat. Off. . |
| 0351344 | 1/1990 | European Pat. Off. . |
| 2191914 | 2/1974 | France . |
| 2142375 | 1/1985 | United Kingdom . |

*Primary Examiner*—Randall L. Green
*Assistant Examiner*—Rob Clarke
*Attorney, Agent, or Firm*—Young & Thompson

[57] ABSTRACT

Transfusion and perfusion device having two pressure bags communicating via a calibrated pressure-reducing valve, each pressure bag including an inflatable pressure balloon. Each balloon is held in an envelope and has the same shape as its envelope. An inflating device provides for the inflation of the pressure balloon, and a verticalization device ensures verticality of the drip. Both envelopes which hold the two balloons are flexible and are each provided with a sleeve intended to receive a flexible pouch of the perfusion product in such a way that the pressure balloon contained in its envelope may be inflated to a high pressure and therefore may act as a pressing balloon in order to provide the flow rate necessary for life support. The invention is applicable to the medical and veterinary fields.

6 Claims, 6 Drawing Sheets

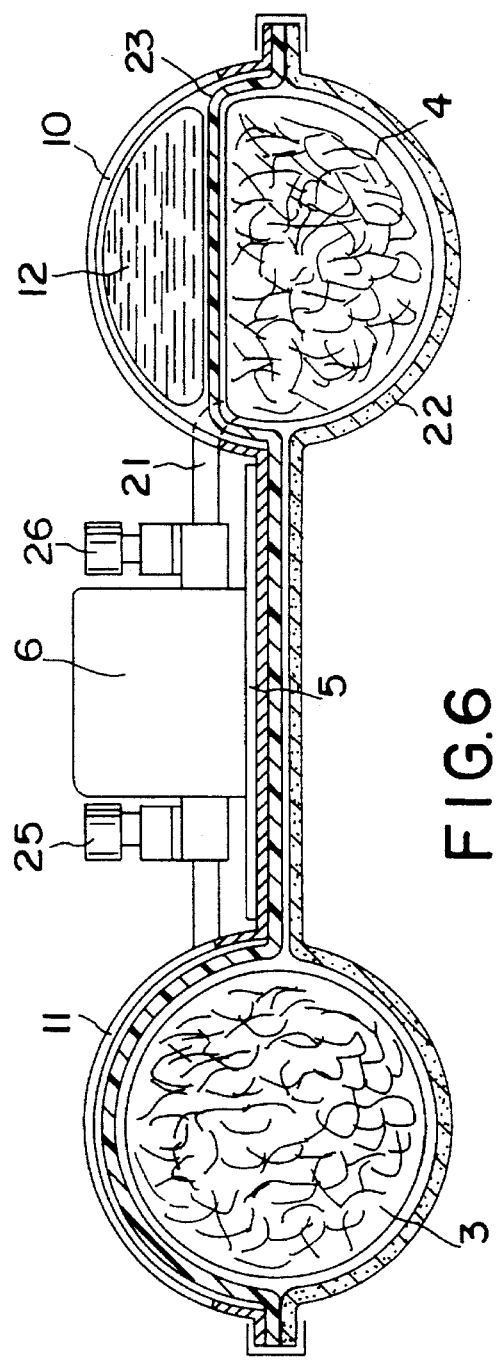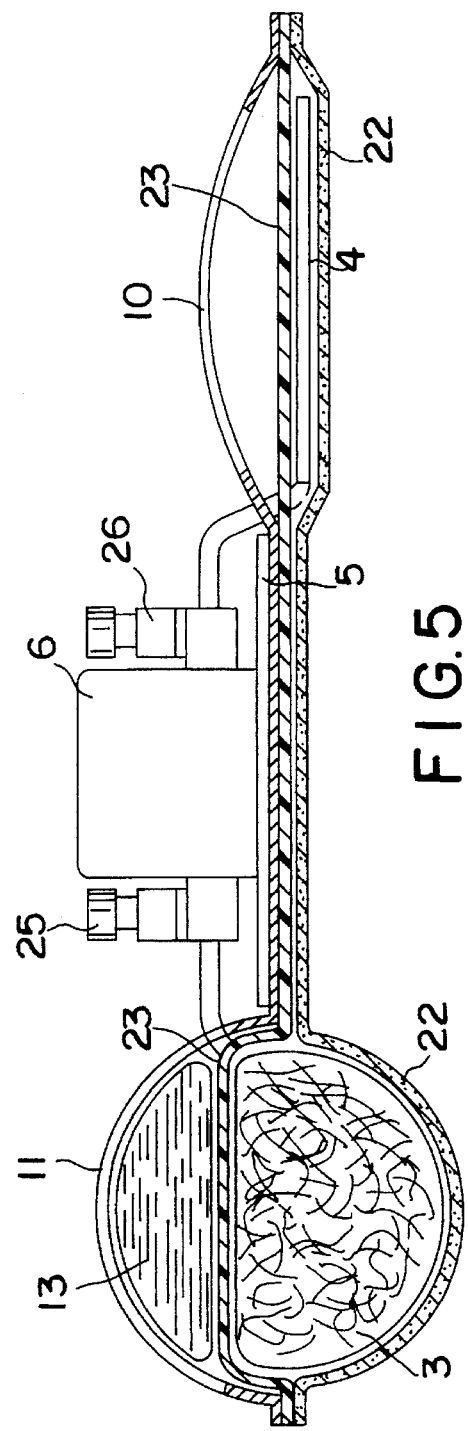

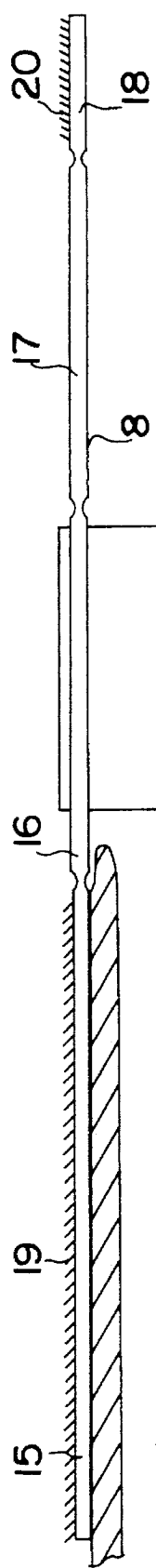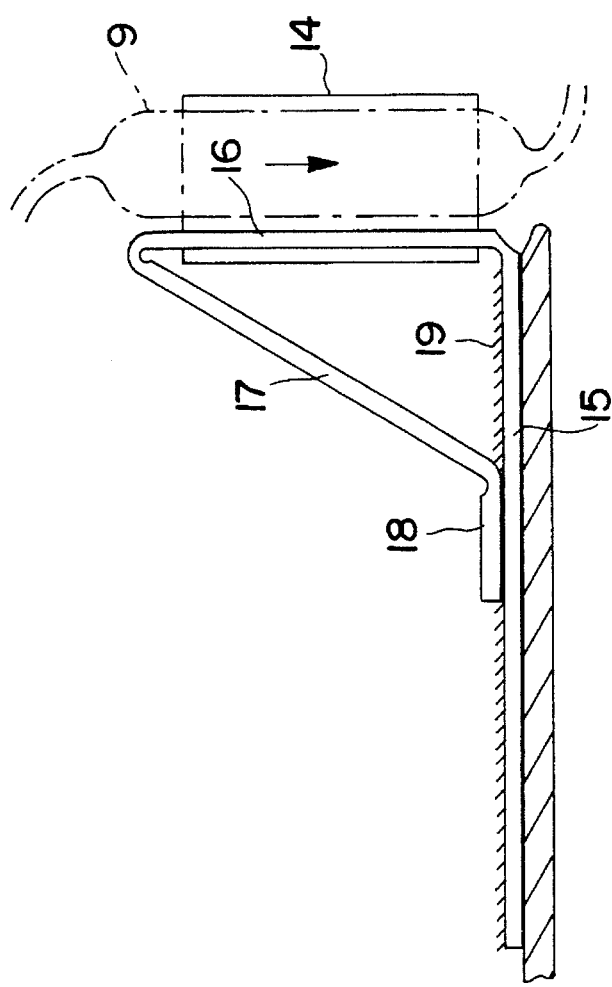

5,496,303

TRANSFUSION AND PERFUSION DEVICE FOR DRIP AND/OR EMERGENCY INTERVENTION

BACKGROUND OF THE INVENTION

1. Field of the Invention

The invention relates to a perfusion device for perfusion bags of blood or solution; the pressurization means is portable and automatic, with double pressure balloons, and whose drip is provided with means ensuring its verticality.

The invention permits two types of perfusion. Conventional slow perfusion, with automatic constant pressure or drip and emergency rapid perfusion under high pressure.

The device permits using the two types of perfusion or simultaneously transfusion.

The parenteral perfusion device is portable and automatic, with air pressure adjusted by an expansion valve for one of the balloons.

This autonomous perfuser can be fixed to the subject or to the immediate environs; it operates by closed circuit, it is independent of gravity and atmospheric pressure.

The balloon which is not under regulated air pressure can permit injection, for example of blood, under very high pressure.

The perfusion device also comprises a means to ensure the verticality of the drip, no matter what the position of the perfused subject and/or of the perfuser.

This invention finds application in medical and veterinary fields.

It is a common sight to see a seriously injured person carried on a stretcher or a sick person, receiving perfusion; someone follows the stretcher, carrying at a certain height a pouch of serum or of blood and its perfusion tubing. The solution pouch is situated above the perfused vein to permit gravity flow of the liquid which it contains.

This process has numerous drawbacks which various patents have already attempted to remedy.

2. The State of the Prior Art

Hinck (U.S. Pat. No. 4,090,514 of May 23, 1978) discloses a bladder inflatable by means of a conventional device with a pressure bulb and manometer, used for stretcher cases: the flow of the liquid to be perfused takes place in the usual way dropwise. The Hinck device is adapted to be suspended vertically instead of and in place of a glass bottle adjacent the bed of the patient. Operating by gravity, it serves above all to accelerate the flow: it is not provided to operate in all positions.

The Hinck device comprises but a single pressure bag: it therefore cannot ensure complete regularity of perfusion. Thus, to the extent that the perfusion pouch empties, the pressure of the pressure balloon surrounding the pouch can only decrease, which results in slowing of the speed of flow of the perfused liquid. To overcome this drawback, the operator can either increase the pressure by means of the pressure bulb, or modify the flow rate of the drip, this process is however not automatic and requires continuous surveillance by a third person. In any case, regularity is not ensured and requires human intervention.

The Hinck apparatus does not permit ensuring perfusion over a range of operating pressures, these not being regulable.

Two other patents, Leibinsohn (EP 0 102 012 of Mar. 7, 1984) and Zoratto (EP 0 210 424 of Feb. 4, 1987) include substantially the same elements and do not comprise new inventive elements relative to Hinck.

B. Keime (GB-A-2 165 312 of Apr. 9, 1986) discloses a device with a sealed housing containing the bag of liquid to be perfused, connected to a cartridge of inert gas, by means of an expansion valve. There is a rigid unexpandable housing, therefore equivalent to a device with a single bag, identical in principle to the preceding patents.

The drawbacks connected with the Keime device are as follows:

the use of an inert gas cartridge which gives no clue as to how full it is, in the absence of a cartridge, this device is useless, the tubing of the pouch of solution contained in the sealed housing must pass through the wall by means of a joint or stuffing box subjected to the internal pressure. The sealing of the casing, the deterioration of the joint and the problems inherent in the passage of the tubing are a handicap.

In the third world countries in which the provision of gas cartridges and servicing are chancy, a manual procedure must be found which is better adapted to the practices of the medical profession.

The profusion device for perfusion bags is an improvement on the patent EP 0 351 344 and on French patent 2.631.242, whose capacities it particularly increases.

The device according to the invention permits exerting a sufficient pressure, manually or otherwise, on a flexible pouch of blood or solution to permit a rapid emergency medical or surgical intervention.

The most widespread present practices use suspended pouches but the pressure exerted by atmospheric pressure is often insufficient to ensure the necessary flow rate in major circulatory emergencies, several other processes have been proposed, over which the device of the present invention has numerous advantages.

The slow perfusion device disclosed in the patents cited above ensures a continuous and automatic perfusion for several hours at the same flow rate by establishing a pressure of 100 millibars thanks to two pressure bags communicating by means of a pressure reducer which ensures to a pressure balloon a constant and suitable pressure.

This perfusion device uses the following principle: a reservoir of energy using a compressible and expansible fluid, stores a potential energy sufficient to deliver, as needed, by means of a calibrated expansion valve, a constant and sufficient pressure to a flexible bag of blood or solution and thereby to impose on it normal conditions of all conventional medical perfusions, for a predetermined period of time, without other intervention or reliance on gravity.

This pressure is established in the first bag and regulated to 100 millibars in the second bag. This constant pressure of 100 millibars, if completely suitable for slow and continuous perfusion for several hours, without intervention, does not have a sufficient flow rate to respond to emergencies and hemorrhage or cardiovascular accidents.

To ensure this flow rate and an immediate perfusion, a high pressure is necessary.

The perfusion device which is the object of this new application permits overcoming this drawbacks.

SUMMARY OF THE INVENTION

The invention consists in the modification in the shape and the function of the envelope containing the pressure balloon which serves as a pressure reserve.

The invention also consists in the technical design of the envelopes and the rendering vertical of the drip.

Novel modifications on the known earlier patents FR-A-2.631.242 and EP 0 351 344, of the same inventor, are as follows:

1. the envelope of the bag containing the pressure balloon which serves as a pressure reserve is provided with a sleeve of unstretchable material, fixed on two opposite edges of the envelope, the upper and lower ends remaining free and thus constituting a sleeve in which can be inserted a flexible pouch of injectable product which is thus compressed between the envelope and the folded over portion.

The pressure balloon contained within the envelope of this bag can be inflated to a high pressure to ensure the pressure necessary for lifesaving purposes, the pressure being maintained manually or otherwise, during the perfusion without passing through the pressure regulator. This pressure can be 500 millibars or more.

2. The transfusion and perfusion device thus comprises two envelopes each provided with a sleeve. A single one of the envelopes has its pressure regulated for slow perfusion. The other is adapted for rapid perfusion or transfusion in an emergency.

To this end, the transfusion and perfusion device is of the type constituted by two pressure bags communicating by means of a calibrated expansion valve which is adjustable, each pressure bag is constituted by an expansible inflatable pressure balloon of the same shape as its envelope; said balloon is contained in an envelope, one of the balloons is the pressure balloon (pressure reserve) which continuously supplies the other pressing balloon (regulated pressure), an inflation bulb ensures the inflation of the pressure balloon, a calibrated adjustable expansion valve ensures, for the pressing balloon, the regulation to 100 millibars of the fluid under pressure contained in the pressure balloon, a device ensures the verticality of the drip, characterized by the fact that the two envelopes ensuring the maintenance of the two balloons are each provided with a sleeve of inextensible material adapted to receive the flexible pouch of product to be perfused and this in a manner such that each pressure balloon contained in each envelope can be inflated either to a high pressure and serve as a power pressure balloon to ensure the necessary flow rate for lifesaving purposes, the pressure being arrived at manually or otherwise during the rapid emergency perfusion, or a reserve of pressure for a regulated pressure for the other pressure balloon whose pressure is adjusted for slow perfusion.

According to another embodiment, the pressure bags are constituted by envelopes, these envelopes are constituted by the assembly in a sealed manner of two walls, an upper wall and a lower wall.

The lower wall is of a flexible or rigid material, inextensible, the upper wall which faces the sleeve is of a flexible and stretchable material; the envelope thus formed by the sealed assembly of the edges of the two walls receives a pressing balloon (reserve) or a presser balloon; said balloon is of stretchable material.

Each envelope contains an inflatable balloon. On the surface of the envelope, on the upper stretchable wall and fixed on its two edges, is a transparent flexible sleeve which is inextensible which thus constitutes a sleeve in which can be inserted a flexible bag of blood or of solution between said sleeve and the upper wall of the envelope.

The material is of elastic cloth which constitutes the upper surface of the envelope and which is located facing the transparent sleeve and in contact with it, it is designed to facilitate during inflation the complete bearing against the transparent sleeve and thus the complete evacuation of the flexible perfusion pouch.

The device to ensure verticality of the drip, no matter what the position of the perfused subject and/or of the perfuser, is constituted by a sleeve adapted to maintain the drip, said sleeve being secured to a tongue which serves as an adjustable support as to verticality and can be folded back, said tongue is formed of four parts which fold against each other along bend lines, the first part, the longest, forms the base which is fixed to the pressurization means, this first part is provided with securement means, the second part is bent so as to be as close as possible to the vertical, because it supports the sleeve that maintains the drip, the third part also folds toward the first part, which forms the base, this third part serving as a bearing tongue, so as to be in contact with the securement means of the first part, it serves as a securement means.

Out of use, the different parts fold against each other to occupy the smallest volume.

According to one embodiment, the securement means are so-called "quick connections".

BRIEF DESCRIPTION OF THE DRAWINGS

The accompanying drawings are given by way of non-limiting example. They show a preferred embodiment according to the invention. They permit easily understanding the invention.

FIG. 5 is a view on the line A—A shown in FIG. 4. It shows the arrangement of the balloons and the envelopes and the characteristics of the walls of the envelopes and balloons.

FIG. 6 is a cross-sectional view on the line B—B of FIG. 3.

FIG. 7 is a side view of the support tongue, of the means which ensures the verticality of the drip, flattened out.

FIG. 8 is a view of the support tongue of FIG. 5 but erected with the drip shown in broken lines.

DETAILED DESCRIPTION OF THE INVENTION

Figure 1:
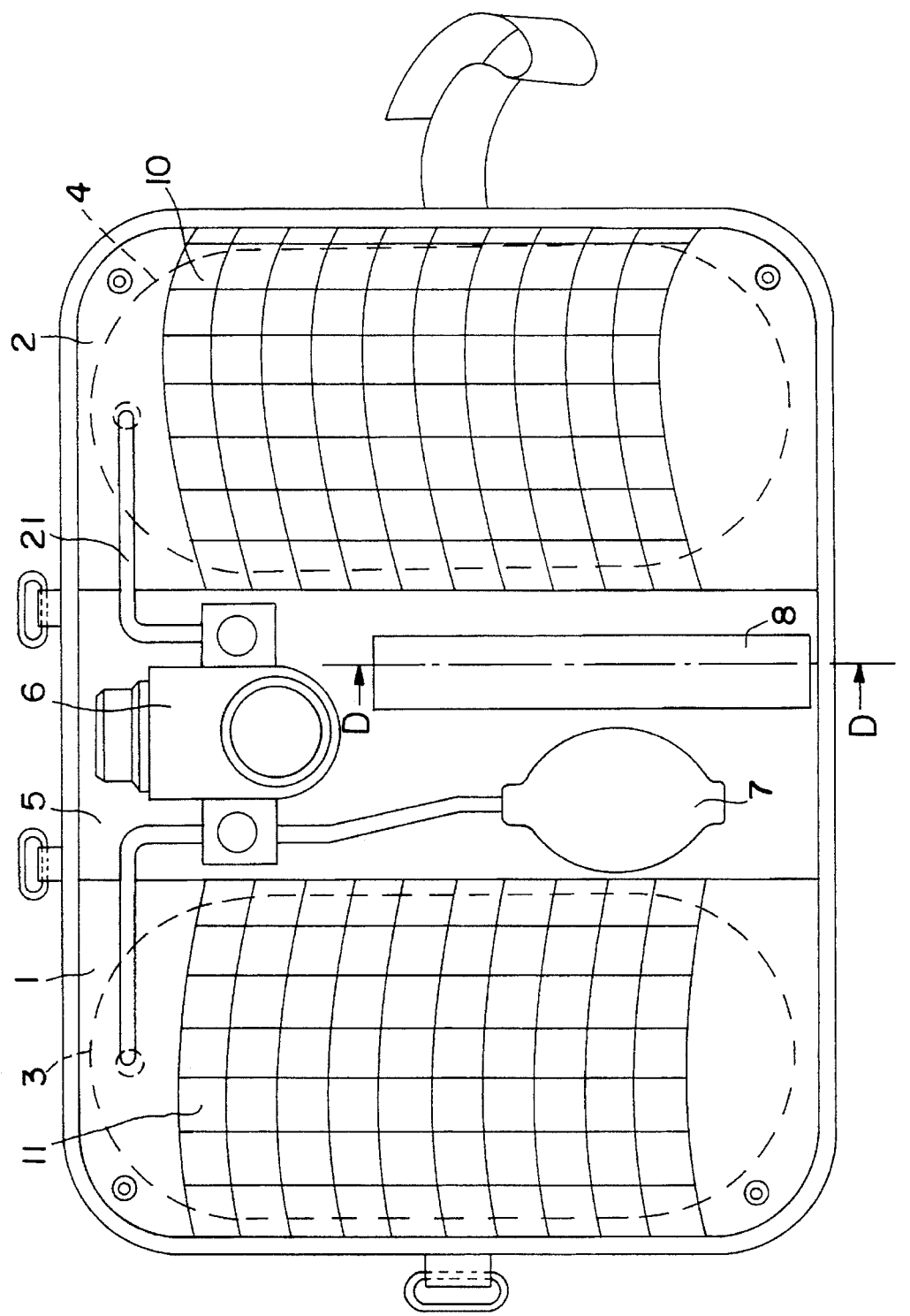
FIG. 1 is a plan view of the perfusion or transfusion device, without the perfusion bag or bags.
Figure 2:
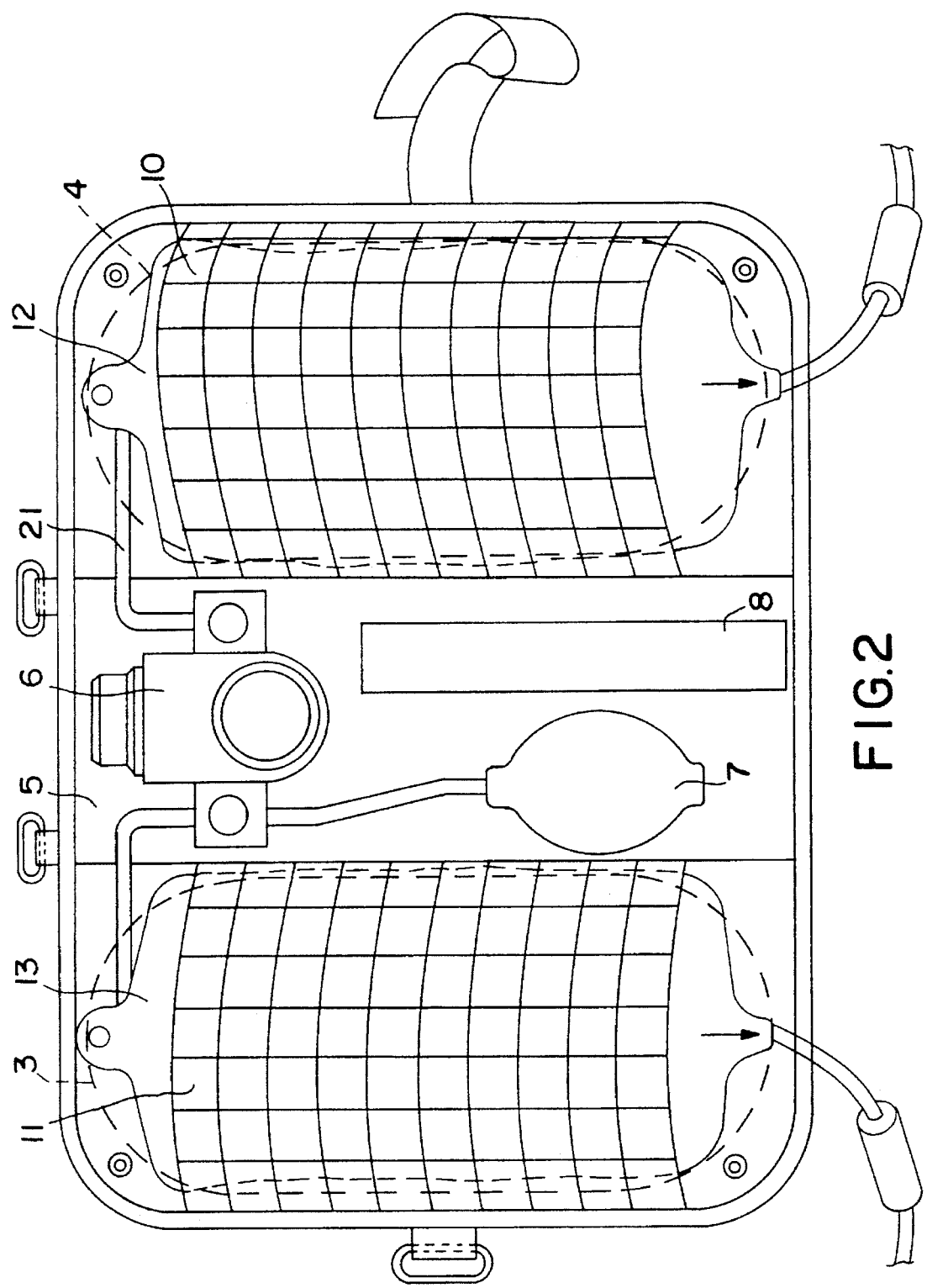
FIG. 2 is a plan view of the perfusion or transfusion device, with the pouches of products to be perfused or transfused, one above the reserve pressure balloon, the other above the pressing balloon, supplied with regulated pressure by the adjustable calibrated expansion valve.
Figure 3:
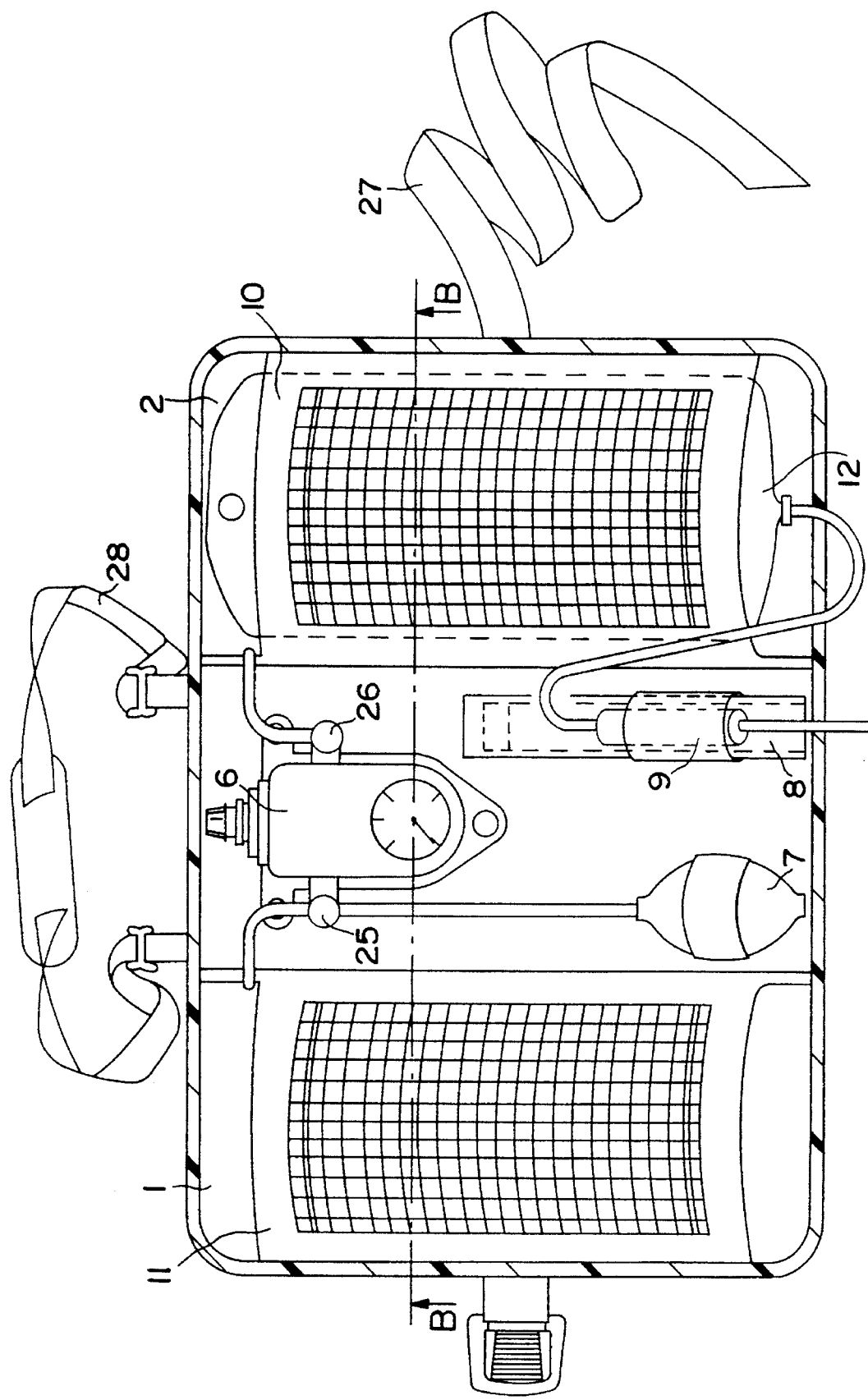
FIG. 3 is a plan view of the device according to another embodiment. In this view, the flexible pouch with product to be transfused or perfused is disposed in the right-hand envelope which contains the pressing balloon for regulated pressure and so serves as a drip.
Figure 4:
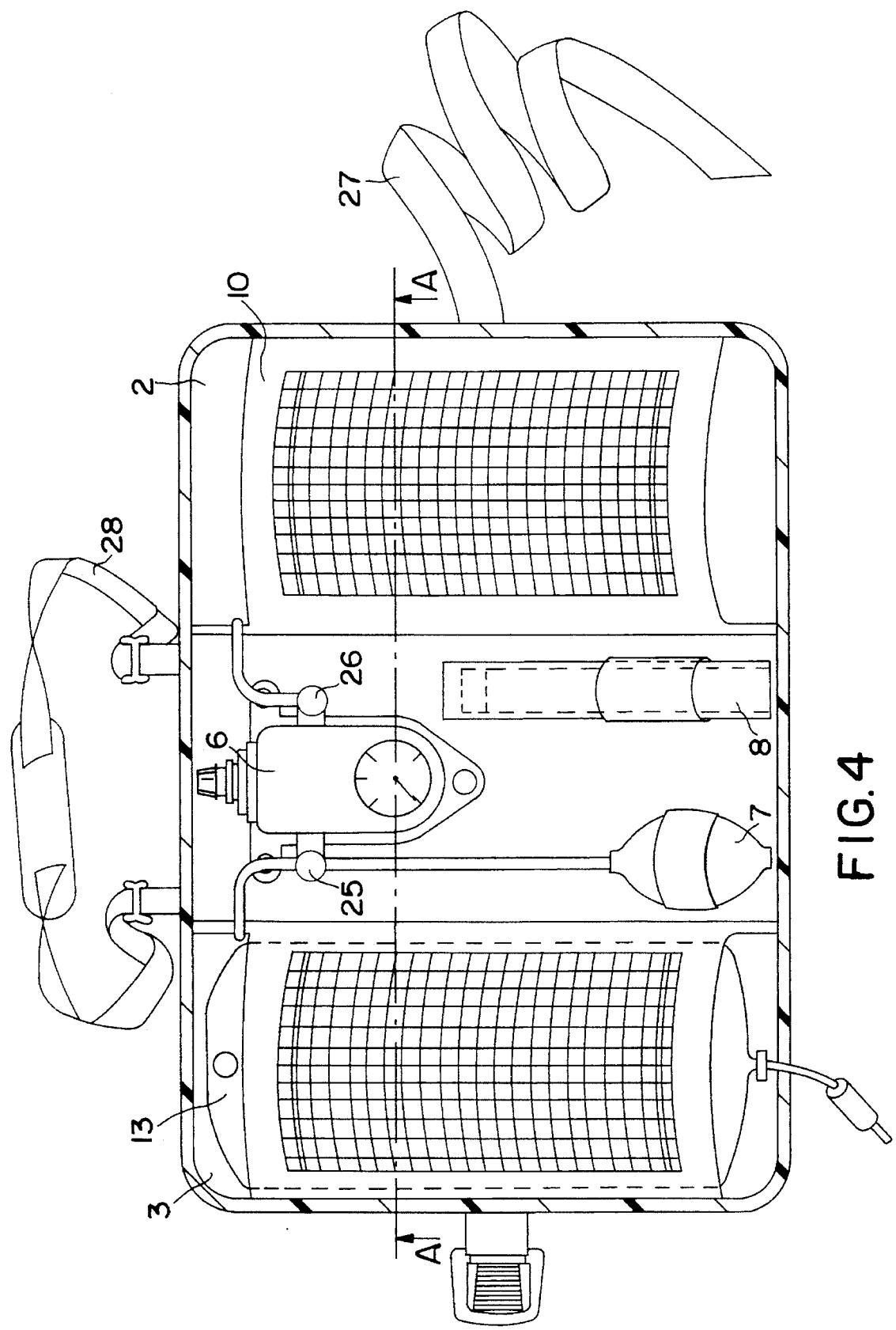
FIG. 4 is a view of the device according to FIG. 3, but in which the flexible pouch of product to be transfused or perfused is disposed in the left envelope which contains the pressure balloon (pressure reserve) for a rapid emergency transfusion.

The two envelopes 1 (left) and 2 (right) are interconnected by a central portion 5 which receives the elements interconnecting the balloons 3 and 4.

The device is constituted by two pressure pockets communicating through a calibrated adjustable expansion valve 6. Each pressure pocket is constituted by a pressure balloon 3, 4 which is stretchable, inflatable, of the same shape as its envelope 1 or 2. Said balloon 3, 4 is contained in an envelope 1, 2. One of the balloons is the pressure balloon 3, the other is the pressing balloon 4. The inflation bulb 7 ensures the inflation of the pressure balloon 3. A verticalization device 8 ensures the verticality of the drip 9.

The two envelopes 1 and 2 providing the support of the two balloons 3, 4 are each provided with a sleeve 10, 11, adapted to receive the flexible pouch 12, 13 of product to be perfused such that the pressure balloon 3 contained in the envelope 1 (left), can be inflated to a high pressure to ensure the necessary flow rate for lifesaving. The pressure is maintained manually or otherwise during the perfusion. The inflation bulb is a manual pump 7, connected by a conduit to the pressure balloon 3 (pressure reserve).

The other envelope 2 (right) contains another balloon 4, the so-called pressing balloon 4, which is connected pressure-wise by a conduit 21 to the calibrated adjustable expansion valve 6. This pressing balloon 4 can therefore be regulated to a pressure of 100 millibars, which permits it to act on the flexible pouch 12 of solution, always with the same pressure, for example 100 millibars, which means that the perfusion will take place at a constant flow rate because the pressure is automatically maintained at 100 millibars, no matter what the filled condition of the pouch of solution and no matter what the flow rate.

According to the embodiment shown in the figures, the sleeves 10 and 11 are constituted by a transparent material, so as to reveal during the course of the perfusion the content of the flexible perfusion pouch, the flexible pouch 12 for the pressing balloon 4, and the flexible pouch 13 for the pressure balloon 3.

As will be easily understood, the pressing balloon 4 will be at a regulated pressure, for example 100 millibars, because it is downstream of the pressure regulator 6, while the pressure balloon 3 is upstream of the pressure regulator 6. This pressure balloon 3 serves as a pressure reserve to supply at a regulated constant pressure the pressing balloon 4 in the case of slow dropwise perfusion.

The pressure balloon 3 can also serve as the power pressure balloon when a flexible perfusion pouch 13 is emplaced between the pressure balloon 3 and the support 11. Of course, this pressure balloon 3 contained in the envelope 1 must be inflated to a high pressure to ensure the flow rate necessary for life saving; the pressure must be maintained manually or otherwise during the rapid emergency perfusion. This pressure can reach 500 millibars or more.

According to a preferred embodiment, the device is constituted by a base 22 of non-elastic flexible cloth on which is secured by welding and cutting a reversible cloth 23 of the same shape and size.

A semi-rigid central portion 5 delimits the two envelopes 1, 2 each partially covered by a sleeve 10, 11 of non-stretch cloth with a transparent window. This sleeve 10, 11 is fixed along its two longitudinal edges only, to leave the possibility of introducing the flexible pouches of products to be transfused or perfused.

The assembly of the device is bordered on its perimeter by a fluorescent braid 24.

Each envelope 1, 2 thus constituted contains a stretchable inflatable balloon 3, 4 whose outlet tubes are connected to a pressure regulator 6 and to the manual inflation bulb 7 or the like disposed on the central semi-rigid portion 5.

Two valves 25, 26 ensure the decompression of the balloons 3, 4 to permit changing the perfusion pouches.

The central portion also supports the verticalization device.

The device is provided with an abdominal strap 27 and with an adjustable neck band 28.

This invention by virtue of its design substantially improves the comfort and autonomy of sick people by eliminating the stand or the person which supports the serum bottle, because the device is secured to the patient or immediately adjacent the patient and operates in all positions.

The verticalization device to ensure the verticality of the drip 9, no matter what the position of the perfused subject and/or of the perfuser, is constituted by a sleeve 14 adapted to support the drip 9.

This sleeve 14 is secured to a tongue 8 which is in four parts 15, 16, 17 and 18. This tongue 8 serves as a foldable support for the drip 9.

Said tongue 8 is formed of four parts 15, 16, 17, 18 which fold relative to each other about bend lines. The first part 15, the longest, forms the base which is fixed to the pressurization means, for example, in the central portion 5 which receives the connection elements between the two balloons 3 and 4. This first part 15 is provided with securement means 19. The second part 16 is folded so as to be as close as possible to the vertical, because it supports the sleeve which supports the drip 9. The third part 17 is also folded toward the first part 15, which forms the base. This third part 17 serves as the bearing tongue. Finally, the fourth part 18 also folds against the first part 15 so as to be in contact with the securement means 19 of said first part 15. This fourth part 18 can itself comprise its own securement means 20, which coact with the securement means 19 of the first part 15.

These securement means 19, 20 can be so-called "quick coupling" devices.

The adjustable pressure regulating valve 6 described above is designed to provide a pressure adjusted to 100 millibars which is the usual pressure for intravenous perfusion. This expansion valve is adjustable and permits varying this pressure downstream, in the pressing balloon 4, as needed. It could be increased or decreased.

REFERENCES 1. 2. Envelopes
3. Pressure balloon
4. Pressing balloon
5. Central portion
6. Expansion valve
7. Manual pump
8. Tongue
9. Drip
10. 11. Sleeves
12. Flexible pouch of the pressing balloon
13. Flexible pouch of the pressure balloon
14. Sleeve of the means to ensure the verticality of the drip
15. 16. 17. 18. Portions of the tongue
19. 20. Attachments
21. Conduit
22. Flexible unstretchable cloth base (lower part of the envelope)
23. Stretchable cloth (upper wall of the envelope)

24. Fluorescent braid
25, 26. Valves
27. Abdominal strap
28. Neck band

I claim:

1. Device for intravenous and intra-arterial transfusion and perfusion securable to a subject and operating in closed circuit, comprising two pressure pockets communicating via a calibrated adjustable expansion valve, each pressure pocket being comprised of a balloon contained in an envelope, each said balloon being stretchable and inflatable and of the same shape as its envelope; one of the balloons functioning as a pressure balloon, and the other balloon functioning as a pressing balloon, said pressure balloon continuously supplying the pressing balloon, an inflation bulb for inflating the pressure balloon, an adjustable calibrated expansion valve for regulating fluid under pressure contained in the pressing balloon to a pressure of 100 millibars, a verticalization device for ensuring a vertical drip, each of said envelopes having a sleeve of unstretchable material adapted to receive a flexible pouch of product to be perfused, whereby the pressure balloon contained in its envelope can be inflated either to a high pressure and thus serve as a power pressing balloon to ensure the flow necessary for lifesaving, or as a pressure reserve for regulated pressure for the other pressing balloon contained in the other envelope.

2. The device according to claim 1, wherein the envelopes are comprised of a sealed assembly of edges of two walls, an upper wall facing the sleeve, and a lower wall; the lower wall being of flexible or rigid unstretchable material, and the upper wall being of flexible and stretchable material; and each of said balloon being of extensible material.

3. The device according to claim 2, wherein each sleeve is flexible transparent but unstretchable, and is located on the upper flexible wall and secured along its edges, said sleeve adapted to receive a flexible bag of blood or of solution between said sleeve and the upper wall of the envelope.

4. The device according to claim 1, wherein the verticalization device includes a sleeve member adapted to support the drip, said sleeve member being fixed to a tongue which serves as an adjustable support, said tongue being formed in four parts which fold relative to each other about bend lines, a first part forming a base and having securement means, a second part being foldable for vertically supporting the sleeve member of the drip, a third part foldable towards the first part and serving as a bearing tongue, and a fourth part foldable against the first part for contacting the securement means of the first part.

5. The device according to claim 4, wherein the securement means are so-called "quick coupling" devices.

6. The device according to claim 4, wherein the fourth part includes its own securement means.

* * * * *